United States Patent
Reiley et al.

(10) Patent No.: US 9,956,013 B2
(45) Date of Patent: May 1, 2018

(54) SYSTEMS AND METHODS FOR THE FIXATION OR FUSION OF BONE

(71) Applicant: SI-BONE INC., San Jose, CA (US)

(72) Inventors: Mark A. Reiley, Washington, DC (US); John T. Lopez, Boulder, CO (US)

(73) Assignee: SI-BONE INC., San Jose, CA (US)

(*) Notice: Subject to any disclaimer, the term of this patent is extended or adjusted under 35 U.S.C. 154(b) by 0 days. days.

(21) Appl. No.: 15/461,304

(22) Filed: Mar. 16, 2017

(65) Prior Publication Data

US 2017/0181770 A1 Jun. 29, 2017

Related U.S. Application Data

(60) Division of application No. 12/930,791, filed on Jan. 18, 2011, now Pat. No. 9,622,783, which is a division
(Continued)

(51) Int. Cl.
*A61B 17/68* (2006.01)
*A61F 2/30* (2006.01)
(Continued)

(52) U.S. Cl.
CPC .......... *A61B 17/72* (2013.01); *A61B 17/1615* (2013.01); *A61B 17/1671* (2013.01); *A61B 17/1682* (2013.01); *A61B 17/68* (2013.01); *A61B 17/866* (2013.01); *A61F 2/30771* (2013.01); *A61F 2/4225* (2013.01); *A61F 2/4455* (2013.01); *A61B 2017/564* (2013.01); *A61F 2002/305* (2013.01); *A61F 2002/3023* (2013.01); *A61F 2002/3082* (2013.01); *A61F 2002/3085* (2013.01); *A61F 2002/30153* (2013.01); *A61F 2002/30156* (2013.01); *A61F 2002/30179* (2013.01); *A61F 2002/30405* (2013.01); *A61F 2002/30777* (2013.01); *A61F 2002/30785* (2013.01); *A61F 2002/30841* (2013.01); *A61F 2002/4238* (2013.01)

(58) Field of Classification Search
CPC ...... A61B 17/68; A61B 17/1671; A61B 17/72
See application file for complete search history.

(56) References Cited

U.S. PATENT DOCUMENTS 1,951,278 A 3/1934 Ericsson
2,136,471 A 11/1938 Schneider
(Continued)

FOREIGN PATENT DOCUMENTS

CN 1128944 A 8/1996
CN 1190882 A 8/1998
(Continued)

OTHER PUBLICATIONS

Acumed; Acutrak Headless Compressioin Screw (product information); 12 pgs; ©2005; retrieved Sep. 25, 2014 from http://www.rcsed.ac.uk/fellows/Ivanrensburg/classification/surgtech/acumed/manuals/acutrak-brochure%200311.pdf.
(Continued)

*Primary Examiner* — Christian Sevilla
(74) *Attorney, Agent, or Firm* — Shay Glenn LLP

(57) ABSTRACT

Various bone fixation/fusion devices are sized and configured to be placed across fracture fragments or between bones that are to be fused.

5 Claims, 16 Drawing Sheets

Related U.S. Application Data of application No. 11/653,504, filed on Jan. 16, 2007, now abandoned, which is a continuation-in-part of application No. 11/136,141, filed on May 24, 2005, now Pat. No. 7,922,765, which is a continuation-in-part of application No. 10/914,629, filed on Aug. 9, 2004, now abandoned.

(51) Int. Cl.
    *A61F 2/44*    (2006.01)
    *A61F 2/42*    (2006.01)
    *A61B 17/16*   (2006.01)
    *A61B 17/86*   (2006.01)
    *A61B 17/72*   (2006.01)
    *A61B 17/56*   (2006.01)

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A * | 11/1988 | Sodhi ............... A61B 17/742 606/67 |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholteh et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A * | 6/1998 | Perry ............... A61B 17/1725 606/62 |
| 5,766,252 A * | 6/1998 | Henry ............... A61F 2/4455 606/247 |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,053,916 A | 4/2000 | Moore |
| 6,056,749 A | 5/2000 | Kuslich |
| 6,086,589 A | 7/2000 | Kuslich et al. |
| 6,096,080 A | 8/2000 | Nicholson et al. |
| 6,120,504 A | 9/2000 | Brumback et al. |
| 6,143,031 A | 11/2000 | Knothe et al. |
| 6,197,062 B1 | 3/2001 | Fenlin |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 * | 10/2001 | Michelson ........ A61F 2/30744 606/247 |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 * | 3/2003 | Warburton ........ A61B 17/164 606/62 |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |

(56) References Cited

U.S. PATENT DOCUMENTS

| | | |
|---|---|---|
| 6,579,293 B1* | 6/2003 | Chandran .......... A61B 17/1725 606/62 |
| 6,582,431 B1 | 6/2003 | Ray |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,723,099 B1 | 4/2004 | Goshert |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,991,461 B2 | 1/2006 | Gittleman |
| 7,118,579 B2 | 10/2006 | Michelson |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,837,735 B2 | 11/2010 | Malone |
| 7,850,732 B2 | 12/2010 | Heinz |
| 7,857,832 B2 | 12/2010 | Culbert et al. |
| 7,887,565 B2 | 2/2011 | Michelson |
| 7,909,832 B2 | 3/2011 | Michelson |
| 7,922,765 B2 | 4/2011 | Reiley |
| 7,942,879 B2 | 5/2011 | Christie et al. |
| 8,062,365 B2 | 11/2011 | Schwab |
| 8,066,705 B2 | 11/2011 | Michelson |
| 8,066,709 B2 | 11/2011 | Michelson |
| 8,142,481 B2 | 3/2012 | Warnick |
| 8,142,503 B2 | 3/2012 | Malone |
| 8,202,305 B2 | 6/2012 | Reiley |
| 8,308,779 B2 | 11/2012 | Reiley |
| 8,388,667 B2 | 3/2013 | Reiley et al. |
| 8,414,648 B2 | 4/2013 | Reiley |
| 8,425,570 B2 | 4/2013 | Reiley |
| 8,444,693 B2 | 5/2013 | Reiley |
| 8,470,004 B2 | 6/2013 | Reiley |
| 8,641,737 B2 | 2/2014 | Matthis et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,858,601 B2 | 10/2014 | Reiley |
| 8,920,477 B2 | 12/2014 | Reiley |
| 8,945,190 B2 | 2/2015 | Culbert et al. |
| 8,986,348 B2 | 3/2015 | Reiley |
| 9,039,743 B2 | 5/2015 | Reiley |
| 9,044,321 B2 | 6/2015 | Mauldin et al. |
| 9,375,323 B2 | 6/2016 | Reiley |
| 9,486,264 B2 | 11/2016 | Reiley et al. |
| 9,492,201 B2 | 11/2016 | Reiley |
| 9,561,063 B2 | 2/2017 | Reiley |
| 9,622,783 B2* | 4/2017 | Reiley .................... A61B 17/68 |
| 9,675,394 B2* | 6/2017 | Reiley .................. A61B 17/846 |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0038123 A1* | 3/2002 | Visotsky ............ A61B 17/8095 606/304 |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0097131 A1 | 5/2003 | Schon et al. |
| 2003/0139815 A1 | 7/2003 | Grooms et al. |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1* | 7/2005 | Zucherman ........ A61B 17/1671 623/17.11 |
| 2005/0159749 A1 | 7/2005 | Levy et al. |
| 2005/0165398 A1 | 7/2005 | Reiley |
| 2005/0192572 A1 | 9/2005 | Abdelgany et al. |
| 2005/0228384 A1 | 10/2005 | Zucherman et al. |
| 2005/0246021 A1 | 11/2005 | Ringeisen et al. |

(56) References Cited

U.S. PATENT DOCUMENTS

| | | |
|---|---|---|
| 2005/0251146 A1 | 11/2005 | Martz et al. |
| 2005/0277940 A1 | 12/2005 | Neff |
| 2006/0036247 A1 | 2/2006 | Michelson |
| 2006/0036251 A1 | 2/2006 | Reiley |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0219634 A1 | 9/2007 | Greenhalgh et al. |
| 2007/0233146 A1 | 10/2007 | Henniges et al. |
| 2007/0250166 A1 | 10/2007 | McKay |
| 2007/0265621 A1 | 11/2007 | Matthis et al. |
| 2007/0270879 A1 | 11/2007 | Isaza et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0109083 A1 | 5/2008 | Van Hoeck et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1 | 7/2008 | Greenhalgh et al. |
| 2009/0043393 A1 | 2/2009 | Duggal et al. |
| 2009/0259261 A1 | 10/2009 | Reiley |
| 2009/0324678 A1 | 12/2009 | Thorne et al. |
| 2010/0022535 A1 | 1/2010 | Lee et al. |
| 2010/0094295 A1 | 4/2010 | Schnieders et al. |
| 2010/0106194 A1 | 4/2010 | Bonutti et al. |
| 2010/0106195 A1 | 4/2010 | Serhan et al. |
| 2010/0131011 A1 | 5/2010 | Stark |
| 2010/0145461 A1 | 6/2010 | Landry et al. |
| 2010/0191292 A1 | 7/2010 | DeMeo et al. |
| 2010/0280619 A1 | 11/2010 | Yuan et al. |
| 2010/0280622 A1 | 11/2010 | McKinley |
| 2011/0029019 A1 | 2/2011 | Ainsworth et al. |
| 2011/0040362 A1 | 2/2011 | Godara et al. |
| 2011/0060375 A1 | 3/2011 | Bonutti |
| 2011/0153018 A1 | 6/2011 | Walters et al. |
| 2012/0179256 A1 | 7/2012 | Reiley |
| 2013/0030529 A1 | 1/2013 | Hunt |
| 2013/0237988 A1 | 9/2013 | Mauldin |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0296953 A1 | 11/2013 | Mauldin et al. |
| 2014/0222150 A1 | 8/2014 | Reiley |
| 2014/0257415 A1 | 9/2014 | Reiley |
| 2014/0276846 A1 | 9/2014 | Mauldin et al. |
| 2014/0276851 A1 | 9/2014 | Schneider et al. |
| 2014/0277462 A1 | 9/2014 | Yerby et al. |
| 2014/0277463 A1 | 9/2014 | Yerby et al. |
| 2014/0288605 A1 | 9/2014 | Mesiwala et al. |
| 2014/0330382 A1 | 11/2014 | Mauldin |
| 2015/0005832 A1 | 1/2015 | Reiley |
| 2015/0105828 A1 | 4/2015 | Reckling et al. |
| 2015/0238205 A1 | 8/2015 | Reiley |
| 2015/0250595 A1 | 9/2015 | Mauldin et al. |
| 2015/0320469 A1 | 11/2015 | Biedermann et al. |
| 2016/0081809 A1 | 3/2016 | Schneider et al. |
| 2016/0081810 A1 | 3/2016 | Reiley et al. |
| 2016/0287171 A1 | 10/2016 | Sand et al. |
| 2016/0302941 A1 | 10/2016 | Reiley et al. |
| 2017/0007409 A1 | 1/2017 | Mauldin et al. |
| 2017/0273729 A1 | 9/2017 | Reiley |
| 2017/0296244 A1 | 10/2017 | Schneider et al. |

FOREIGN PATENT DOCUMENTS

| | | |
|---|---|---|
| CN | 1909848 A | 2/2007 |
| EP | 1287796 A1 | 3/2003 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003533329 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2008540036 A | 11/2008 |
| JP | 2009521990 A | 6/2009 |
| WO | WO97/31517 A2 | 8/1997 |
| WO | WO 01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO 2006/023793 A2 | 3/2006 |

OTHER PUBLICATIONS

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Reiley, Mark A.; U.S. Appl. No. 12/357,483 entitled "Systems and methods for the fixation or fusion of bone in the hand and wrist," filed Jan. 22, 2009 (abandoned).

* cited by examiner

SYSTEMS AND METHODS FOR THE FIXATION OR FUSION OF BONE

CROSS REFERENCE TO RELATED APPLICATIONS

This application is a divisional of U.S. application Ser. No. 12/930,791, filed Jan. 18, 2011, which is a divisional of U.S. application Ser. No. 11/653,504, filed Jan. 16, 2007, (now abandoned), which is a continuation-in-part of U.S. application Ser. No. 11/136,141, filed May 24, 2005, now U.S. Pat. No. 7,922,765, which is a continuation-in-part of U.S. application Ser. No. 10/914,629, filed Aug. 9, 2004 (now abandoned).

FIELD OF THE INVENTION

This application relates generally to the fixation of bone.

BACKGROUND OF THE INVENTION

Many types of hardware are available both for fracture fixation and for the fixation of bones that are to be fused (arthrodesed).

Metal and absorbable screws are routinely used to fixate bone fractures and osteotomies. It is important to the successful outcome of the procedure that the screw is able to generate the compressive forces helpful in promoting bone healing.

SUMMARY OF THE INVENTION

The invention provides bone fixation/fusion devices and related methods for stabilizing bone segments, which can comprise parts of the same bone (e.g., fracture fixation) or two or more individual bones (e.g., fusion). The systems and methods include a fixation/fusion device adapted for placement in association with bone segments.

One aspect of the invention provides a bone fixation/fusion device comprising a body adapted for placement in association with a fracture line or between different bone segments, and at least one fixation ridge on the body.

In one embodiment, the fixation ridge includes a curvilinear portion.

In one embodiment, there are at least two spaced-apart fixation ridges on the body. In one arrangement, the separation distance between the fixation ridges remains essentially the same from one end of the fixation ridges toward an opposite end of the fixation ridges. In another arrangement, the separation distance between the fixation ridges changes from one end of the fixation ridges toward an opposite end of the fixation ridges.

In one embodiment there is a pair of cylindrical end caps on the body.

Another aspect of the invention provides a flexible bone fixation/fusion device.

In one embodiment, there are holes extending through the body. In one arrangement, the holes extend perpendicularly from the top to the bottom of the body. In another arrangement, the holes extend angularly from the top to the bottom of the body. In another arrangement, the holes extend perpendicularly from one side of the body to the other side of the body. In another arrangement, the holes extend angularly from one side of the body to the other side of the body.

In another embodiment, the body is formed with a hollow cavity.

In another embodiment, the body of the bone fixation/fusion device is formed in an accordion-type configuration.

Another aspect of the invention provides methods for placing a bone fixation/fusion device in bone.

One representative method provides a bone fixation/fusion device comprising a body and at least one fixation ridge on the body including a curvilinear portion. The method forms a bone cavity in a selected bone site including at least one slot in the bone cavity sized and configured to receive the fixation ridge. The method inserts the body in the bone cavity with the fixation ridge nesting within the slot.

In one embodiment, the selected bone site comprises a first bone segment, a second bone segment, and a non-bony region comprising an interruption between the first and second bone segments. In this embodiment, the representative method forms a first bone cavity in the first bone segment and a second bone cavity in the second bone segment across the interruption from the first bone cavity. The representative method forms in at least one of the first and second bone cavities at least one slot sized and configured to receive the fixation ridge. In this arrangement, the representative method inserts the body in the first bone cavity, the second bone cavity, and the interruption, with the fixation ridge nesting within the slot to apply compression between the first and second bone segments.

Another representative method provides a bone fixation/fusion device comprising a body and first and second spaced-apart fixation ridges on the body. The representative method forms a bone cavity in a selected bone site including first and second slots sized and configured to receive the first and second fixation ridges, respectively. In this arrangement, the representative method inserts the body in the bone cavity with the first and second fixation ridges nested within the first and second slots.

In one embodiment, the selected bone site comprises a first bone segment, a second bone segment, and a non-bony region comprising an interruption between the first and second bone segments. In this embodiment, the representative method forms a first bone cavity in the first bone segment including a first slot sized and configured to receive the first fixation ridge. The representative method also forms a second bone cavity in the second bone segment across the interruption from the first bone cavity, including forming a second slot sized and configured to receive the second fixation ridge. In this arrangement, the representative method inserts the body in the first bone cavity, the second bone cavity, and the interruption, with the first and second fixation ridges nesting within the first and second slots, respectively.

Another representative method provides a bone fixation/fusion device comprising a body and first and second fixation ridges on the body. The first and second fixation ridges are separated by a ridge separation distance. The representative method selects a bone site comprising a first bone segment, a second bone segment, and a non-bony region comprising an interruption between the first and second bone segments. The representative method forms a first bone cavity in the first bone segment including a first slot sized and configured to receive the first fixation ridge. The representative method forms a second bone cavity in the second bone segments across the interruption from the first bone cavity including a second slot sized and configured to receive the second fixation ridge. The first and second slots are separated by a slot separation distance that is greater than the ridge separation distance. In this arrangement, the representative method inserts the body in the first bone cavity, the second bone cavity, and the interruption with the first and second fixation ridges nesting within the first and second slots, respectively, to apply compression between the first and second bone segments.

In one embodiment, the selected bone site comprises a first bone segment, a second bone segment, and a non-bony region comprising an interruption between the first and second bone segments. In this embodiment, the representative method forms a first bone cavity in the first bone segment including a first cylindrical aperture sized and configured to receive the first cylindrical end cap. The representative method forms a second bone cavity in the second bone segments across the interruption from the first bone cavity including a second cylindrical aperture sized and configured to receive the second cylindrical end cap. In this arrangement, the representative method inserts the body in the first bone cavity, the second bone cavity, and the interruption with the first and second end caps nesting within the first and second apertures, respectively.

Another representative method provides a bone fixation/fusion device comprising a body and first and second cylindrical end caps on the body. The center points of the first and second cylindrical end caps are separated by an end cap distance. The representative method selects a bone site comprising a first bone segment, a second bone segment, and a non-bony region comprising an interruption between the first and second bone segments. The representative method forms a first bone cavity in the first bone segment including a first cylindrical aperture sized and configured to receive the first cylindrical end cap. The representative method forms a second bone cavity in the second bone segments across the interruption from the first bone cavity including a second cylindrical aperture sized and configured to receive the second cylindrical end cap. The first and second slots are separated by an aperture separation distance that is greater than the end cap separation distance. In this arrangement, the representative method inserts the body in the first bone cavity, the second bone cavity, and the interruption with the first and second end caps nesting within the first and second apertures, respectively, to apply compression between the first and second bone segments.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

Figure 1A:
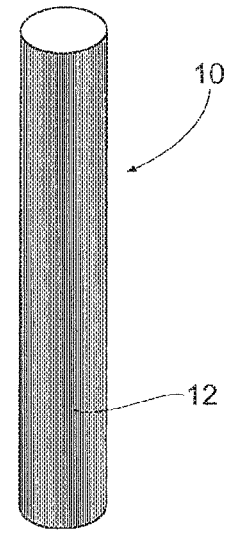
FIGS. 1A and 1B are perspective alternative views of a bone fixation/fusion device having a bony in-growth and/or through-growth region of a mesh configuration.
Figure 1B:
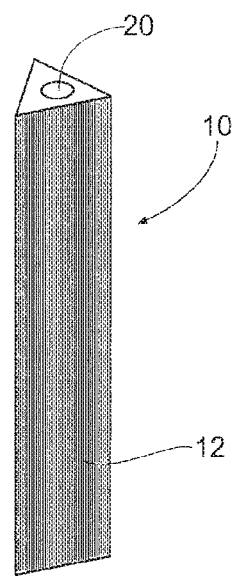

FIGS. 1A and 1B show representative alternative configurations of a device 10 sized and configured for the fixation of bone fractures (i.e., fixation of parts of the same bone) or for the fixation of bones which are to be fused (arthrodesed) (i.e., fixation of two or more individual bones that are adjacent and/or jointed). For the sake of shorthand, the device will sometimes be called a bone fixation/fusion device, to indicate that it can perform a fixation function between two or more individual bones), or a fusion function between two or more parts of the same bone, or both functions. As used herein, "bone segments" or "adjacent bone regions" refer to either situation, i.e., a fracture line in a single bone or a space between different bone segments.

In the embodiments shown in FIGS. 1A and 1B, the bone fixation/fusion device 10 comprises an elongated, stem-like structure. The device 10 can be formed—e.g., by machining, molding, or extrusion—from a material usable in the prosthetic arts, including, but not limited to, titanium, titanium alloys, tantalum, chrome cobalt, surgical steel, or any other total joint replacement metal and/or ceramic, sintered glass, artificial bone, any uncemented metal or ceramic surface, or a combination thereof. Alternatively, the device 10 may be formed from a suitable durable biologic material or a combination of metal and biologic material, such as a biocompatible bone-filling material. The device 10 may be molded from a flowable biologic material, e.g., acrylic bone cement, that is cured, e.g., by UV light, to a non-flowable or solid material.

The bone fixation/fusion device 10 can take various shapes and have various cross-sectional geometries. The device 10 can have, e.g., a generally curvilinear (i.e., round or oval) cross-section—as FIG. 1A shows—or a generally rectilinear cross section (i.e., square or rectangular or triangular—as FIG. 1B shows for purposes of illustration), or combinations thereof. As will be described in greater detail later (see, e.g., FIGS. 21A to 21F), instead of being shaped like an elongated stem, the body of the bone fixation/fusion device 10 can be less elongated and form more of a flattened, "wafer" configuration, having, e.g., a rectangular, square, or disc shape.

Figure 3:
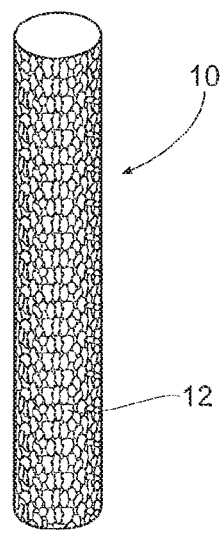
FIG. 3 is a perspective view of an alternative embodiment of a bone fixation/fusion device having a bony in-growth and/or through-growth region of a trabecular configuration.
Figure 2:
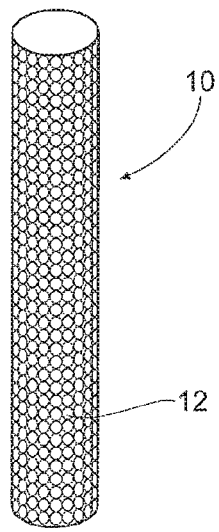
FIG. 2 is a perspective view of an alternative embodiment of a bone fixation/fusion device having a bony in-growth and/or through-growth region of a beaded configuration.

As FIGS. 2 and 3 show, the bone fixation/fusion device 10 desirably includes a region 12 formed along at least a portion of its length to promote bony in-growth onto or into surface of the device 10 and/or bony growth entirely through all or a portion of the device 10.

The region 12 can comprise, e.g., through holes, and/or various surface patterns, and/or various surface textures, and/or pores, or combinations thereof. The device 10 can be coated or wrapped or surfaced treated to provide the bony in-growth or through-growth region 12, or it can be formed from a material that itself inherently possesses a structure conducive to bony in-growth or through-growth, such as a porous mesh, hydroxyapetite, or other porous surface. The device 10 may further be covered with various other coatings such as antimicrobial, antithrombotic, and osteoinductive agents, or a combination thereof. The region 12 may be impregnated with such agents, if desired.

The configuration of the region 12 can, of course, vary. By way of examples, FIG. 1 shows the region 12 as an open mesh configuration; FIG. 2 shows the region 12 as beaded configuration; and FIG. 3 shows the region as a trabecular configuration. Any configuration conducive to bony in-growth and/or bony through-growth will suffice.

Figure 4:
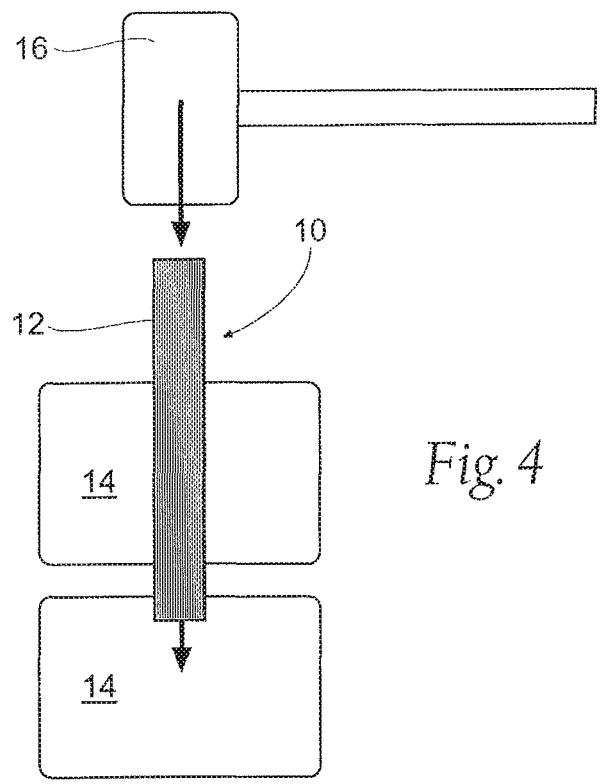
FIG. 4 is a schematic view of a bone fixation/fusion device of the type shown in FIG. 1, being inserted in association with bone across a fracture line or between different bone segments.

In use (see FIGS. 4 and 5), the bone fixation/fusion device 10 is inserted into a space between two adjacent bone surfaces, e.g., into a fracture site in a single bone or between two bones (e.g., adjacent vertebral bodies) which are to be fused together. In FIG. 4, the device 10 is shown being tapped into bone through bone segments 14 (i.e., across a fracture line or between adjacent bones to be fused) with a tap 16. The bone may be drilled first to facilitate insertion of the device 10. The bony in-growth or through-growth region 12 along the surface of the device 10 accelerates bony in-growth or through-growth onto, into, or through the device 10. Bony in-growth or through-growth onto, into, or through the device 10 helps speed up the fusion process or fracture healing time.

Figure 5:
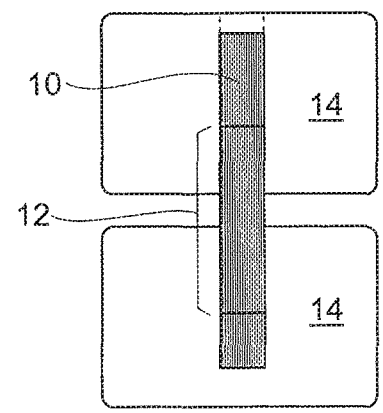
FIG. 5 is a schematic view of a bone fixation/fusion device positioned in association with a fracture line or between different bone segments with a bony in-growth and/or through growth region extending across the fracture line or space between different bone segments.

The bony in-growth or through-growth region 12 may extend along the entire outer surface of the device 10, as shown in FIG. 4, or the bony in-growth or through-growth region 12 may cover just a specified distance on either side of the bone segments or fracture line, as shown in FIG. 5.

The size and configuration of the device 10 can be varied to accommodate the type and location of the bone to be treated as well as individual anatomy.

Figure 6:
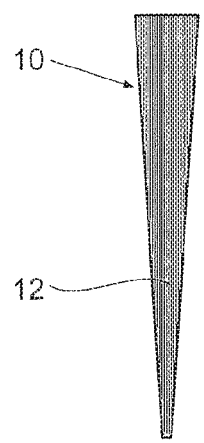
FIG. 6 is a front plan view of an alternative embodiment of a bone fixation/fusion device having a bony in-growth and/or bony through-growth region, in which the device has a conical configuration.
Figure 7:
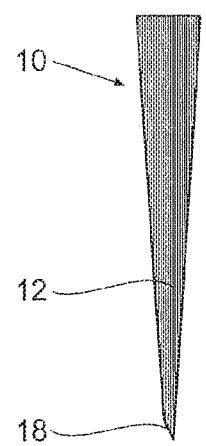
FIG. 7 is a front plan view of an alternative embodiment of a bone fixation/fusion device having a bony in-growth and/or through-growth region in which the device has a beveled distal tip.
Figure 8A:
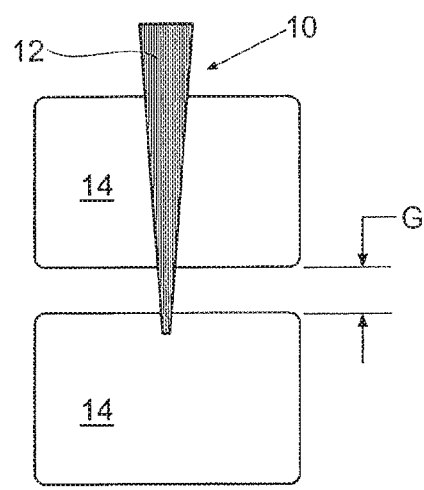
FIGS. 8A and 8B are schematics illustrating the insertion of a bone fixation/fusion device of the type shown in FIG. 6 in association with a fracture line or between different bone segments.
Figure 8B:
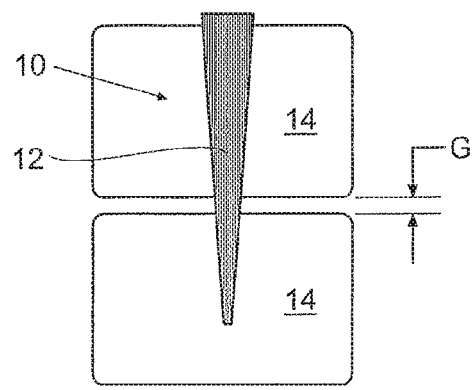

As FIG. 6 shows, the device 10 can be angled or tapered in a conical configuration. The degree of angle can be varied to accommodate specific needs or individual anatomy. A lesser degree of angle (i.e., a more acute angle) decreases the risk of splitting the bone as the device 10 is tapped into the bone or the fracture segments 14. The device 10 may also include a beveled distal tip 18 to further add in insertion of the device 10 into bone, as shown in FIG. 7. As shown in FIGS. 8A and 8B, the conical shape also helps drive the bone segments or fracture fragments together, reducing the gap (G) between the bone segments 14 or fracture segments.

In FIGS. 9 to 12, the device 10 is cannulated, having a central lumen or throughbore 20 extending through it, to assist in the placement of the device 10 within bone. FIG. 1B also shows a cannulated throughbore 20 in a different configuration.

Figure 9:
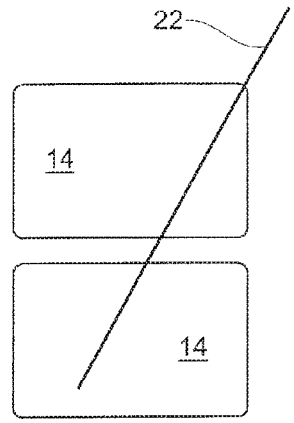
FIG. 9 is a schematic illustrating a guidewire being introduced into bone in association with a fracture line or between different bone segments.
Figure 10:
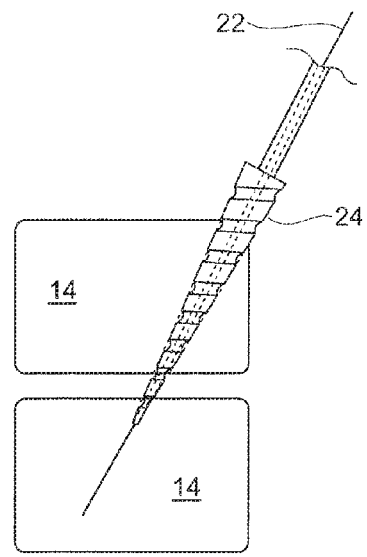
FIG. 10 is a schematic similar to FIG. 9 and illustrating a drill bit being introduced over the guidewire.
Figure 11:
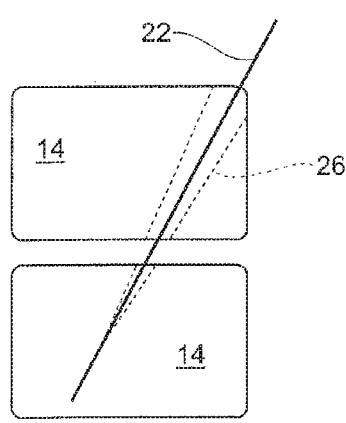
FIG. 11 is a schematic similar to FIG. 10 and illustrating a bore formed in the bone remaining after withdrawal of the drill bit.
Figure 12:
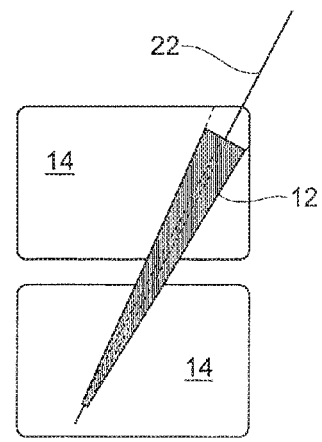
FIG. 12 is a schematic similar to FIG. 11 and illustrating insertion of a bone fixation/fusion device into the pre-formed bore.

In use, the physician can insert a conventional guide pin 22 through the bone segments 14 by conventional methods, as FIG. 9 shows. A cannulated drill bit 24 can then be introduced over the guide pin 22, as seen in FIG. 10. A single drill bit or multiple drill bits 24 can be employed to drill through bone fragments or bone surfaces to create a bore 26 of the desired size and configuration. In the illustrated embodiment, the drill bit 24 is sized and configured to create a conical bore 26 similar in size and configuration to the device 10. The bore 26 is desirably sized and configured to permit tight engagement of the device 10 within the bore 26 and thereby restrict movement of the device 10 within the bore 26. The pre-formed bore 26 may be slightly smaller than the device 10, while still allowing the device 10 to be secured into position within the bore 26 by tapping. As seen in FIG. 11, the drill bit 24 is then withdrawn. The device 10 is then inserted into the bore 26 over the guide pin 22, as FIG. 12 shows. The guide pin 22 is then withdrawn.

Alternatively, the bone fixation/fusion device 10 itself can include screw-like threads along the body for screwing the device into place. In the arrangement, the device 10 may be self-tapping. Also in this arrangement, the device 10 can be cannulated for use with a guide pin 22, or it need not be cannulated.

Multiple devices 10 may be employed to provide additional stabilization. While the use of multiple devices 10 will now be described illustrating the use of multiple devices 10 of the same size and configuration, it is contemplated that the devices 10 may also be of different size and/or configuration, e.g., one device 10 is of a cylindrical configuration and a second device 10 is of a conical configuration.

Figure 13:
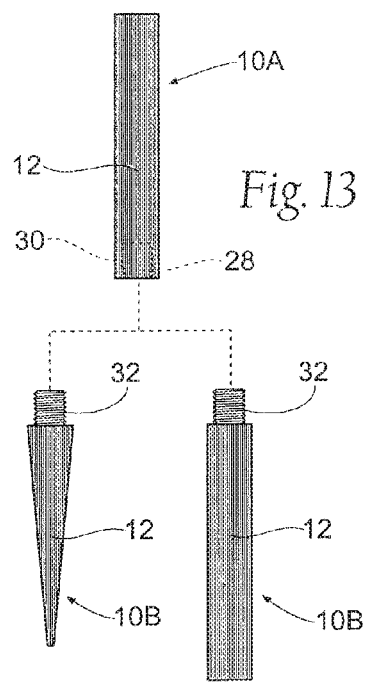
FIG. 13 is an exploded front plan view illustrating the coupling of a pair of bone fixation/fusion by threaded engagement.

In many cases, it may be desirable to couple a series of devices 10 together, e.g., to provide stabilization over a larger surface area. A series of devices 10 may be coupled together be any suitable means, e.g., by a snap fit engagement, or a groove and tab key arrangement, or by a Morse taper fit, or combinations thereof. In one embodiment, a series of devices 10 are coupled by threaded engagement. As illustrated in FIG. 13, a first device 10A includes a recess 28 at one end providing a series of internal threads 30. In the illustrated embodiment, the first device 10 is of a cylindrical configuration, but may be of any desired configuration. The internal threads 30 couple with a series of complementary external threads 32 on a second device 10B of a similar or of a different configuration to couple the first and second devices 10A and 10B together.

Figure 14:
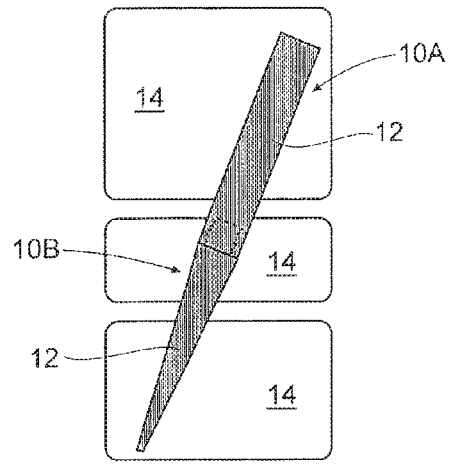
FIG. 14 is a schematic illustrating a pair of bone fixation/fusion devices coupled together and inserted in association with a fracture line or between different bone segments.

The devices 10A and 10B are desirably coupled together prior to being inserted into the pre-formed bore 26. The series of internal and external threads 30 and 32 provide an interlocking mechanism that permits a series of devices 10 to be stacked and connected to cover a larger area or multiple bone segments 14 (e.g., a bone having multiple fractures) and thereby provides additional stabilization, as seen in FIG. 14.

Figure 15:
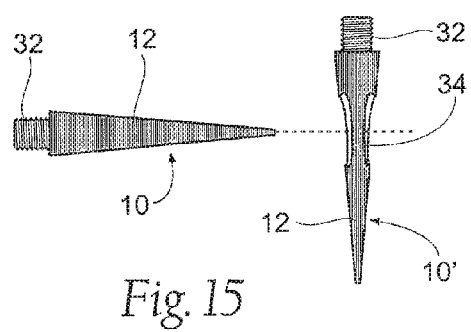
FIG. 15 is a front plan view illustrating passage of a bone fixation/fusion device through a fenestration in another bone fixation/fusion device.

FIG. 15 illustrates another embodiment in which a device 10' includes an opening or fenestration 34 to allow another device 10 to pass through, thereby providing additional stabilization. The fenestration 34 can be sized and configured to permit another device 10 to be passed through the device 10' at virtually any angle. The fenestration 34 can also be sized and configured to limit movement of the second device 10 relative to the second device 10'.

Figure 16:
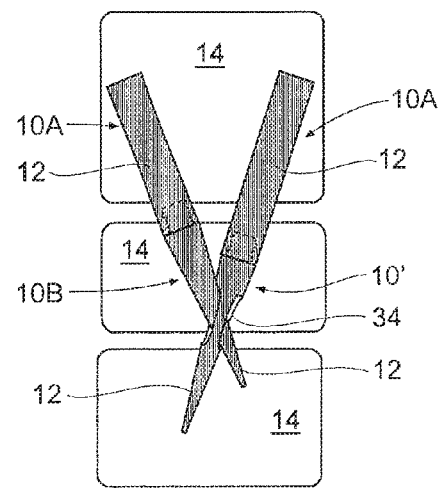
FIG. 16 is a schematic illustrating the placement of a series of bone fixation/fusion devices in bone.

In use, and as shown in FIG. 16, the physician taps a first device 10' having a fenestration 34 through the bone segments. A second device 10 is then inserted (e.g., by tapping) through the fenestration 34 of the first device 10' into place.

It is further contemplated that device 10' may also be adapted for coupling with another device 10A (e.g., by a series of external and internal threads), permitting the devices 10' and 10A to be additionally stacked and connected, as also shown in FIG. 16.

Figure 17:
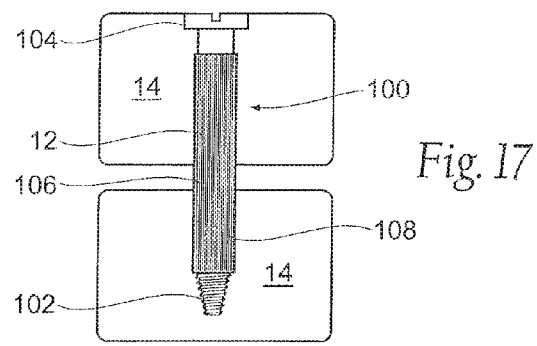
FIG. 17 is a top plan view of a bone fixation/fusion device positioned in association with a fracture line or between different bone segments.

FIG. 17 illustrates an alternative form of a bone fixation/fusion device 100. Similar to the type of bone fixation/fusion device 10 previously described, device 100 includes a body 106 formed of a durable material that is not subject to significant bioabsorption or resorption by surrounding bone or tissue over time. In other words, the body 106 is intended to remain in place for a time sufficient to stabilize the fracture or fusion site. Such materials are well known in the prosthetic arts and include, e.g., titanium, titanium alloys, tantalum, chrome cobalt, surgical steel, or any other total joint replacement metal and/or ceramic, sintered glass, artificial bone, any uncemented metal or ceramic surface, or a combination thereof. Alternatively, the body 106 of the bone fixation/fusion device 100 may be formed from a suitable durable biologic material or a combination of metal and biologic material, such as a biocompatible bone-filling material. The body 106 of the device 100 may be molded from a flowable biologic material, e.g., acrylic bone cement, that is cured, e.g., by UV light, to a non-flowable or solid material.

The body 106 of the device 100 may also include a bony in-growth or through-growth region 108, as already described in association with previous embodiments.

Unlike the bone fixation/fusion device 10, the bone fixation/fusion device 100 includes at least one region associated with the body 106 that, in contrast to the body 106, comprises a material that is subject to more rapid in vivo bioabsorption or resorption by surrounding bone or tissue over time, e.g., within weeks or a few months. The resorbable material can comprise, e.g., polylactic acid (PLA), polyglycolic acid (PGA), poly(lactideglycolide) copolymers, polyanliydrides, cyclode, cirsns, polyorthoasters, n-vinyl alcohol, or other bioabsorbable polymers or like materials known or recognized in the prosthetic arts as having such characteristics. The bioabsorbable region is intended to facilitate implantation or placement of the body 106, but over time be absorbed to minimize the footprint of the implanted device 100 in the long run.

The bioabsorbable region or regions can possess functionality to aid in the implantation process. For example, as shown the illustrated embodiment, there are two bioabsorbable regions 102 and 104. Region 102 comprises a bioabsorbable screw region 102, which is desirably threaded or otherwise suitably configured to pierce bone and facilitate advancement of the device 100 into bone. The other region 104 comprises a bioabsorbable head region 104, which is desirably configured to mate with an installation instrument, e.g., a screwdriver, to further facilitate advancement and positioning of the bone fixation/fusion device 100 in bone. The bioabsorbable head 104 may also be sized and configured to temporarily anchor the device 100 within bone, e.g., the head 104 may be a slightly larger diameter than the body 106 of the device 100. The bioabsorbable screw portion 102 and head portion 104 are configured to provide an immediate benefit during the initial placement or position of the device 100, but over time be resorbed when they have served their initial purpose during implantation. This leaves the more durable and less resorbable body 106 behind, to serve its longer-term function of stabilizing the fracture or fusion site.

Figure 18A:
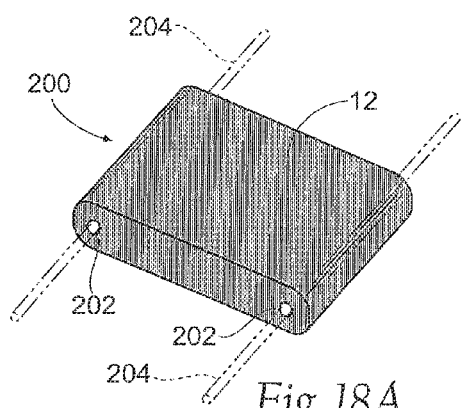
FIG. 18A is a perspective view of an alternative embodiment of a bone fixation/fusion device having a bony in-growth and/or bony through-growth region that extends substantially along the entire device.
Figure 18B:
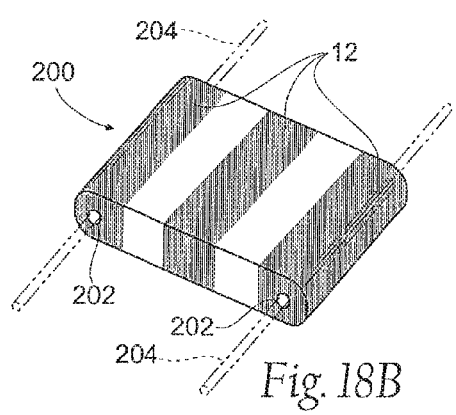
FIG. 18B is a perspective view of a bone fixation/fusion device similar to FIG. 18A and having a bony in-growth and/or bony through-growth region that extends along a portion of the device.

As previously disclosed, a given bone fixation/fusion device can take various shapes and geometries. For example, as shown in FIGS. 18A and 18B, the bone fixation/fusion device 200 possesses a flattened rectangular (or wafer-like) configuration. A region 12 of the device 200 can be textured or treated, as previously described, to provide bony in-growth or through-growth. The bony in-growth or through-growth region 12 may extend along the entire device 200 (see FIG. 18A) or along any portion or portions of the device 200 (see FIG. 18B).

Figure 19:
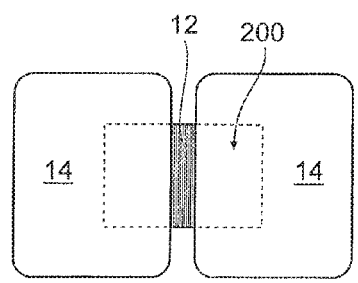
FIG. 19 is a top plan view of the bone fixation/fusion device of FIG. 18A in positioned in association with a fracture line or between different bone segments.
Figure 20:
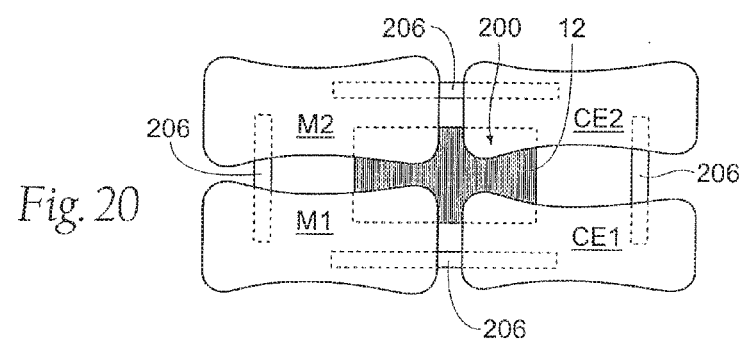
FIG. 20 is a top plan view of the bone fixation/fusion device of FIG. 18A positioned in association with a fracture line or between different bone segments and stabilized by fixation screws.

The bone fixation/fusion device 200 is desirably sized and configured to be positioned to join two or more adjacent bone segments 14 (which can comprise a fracture site, a fusion site, or both), as FIG. 19 shows, to fix and to promote the fusion of the adjacent bone segments 14. The device 200 may also be sized and configured to fix and to promote fusion of multiple bone segments 14 or compound fractures, as FIG. 20 shows. FIG. 20 illustrates placement of the bone fixation/fusion device 200 sized and configured for the fixation and fusion of, for example, a first cuneiform (CE1), a second cuneiform (CE2), a first metatarsal (M1), and a second metatarsal (M2).

As shown in FIG. 20, one or more auxiliary fixation elements, such as conventional orthopedic screws 206, may also be placed within and/or across the bone segments 14 by conventional techniques, to augment the stabilization of the bone segments 14 during the fusion process.

Figure 21A:
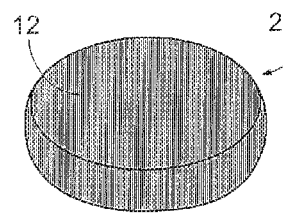
FIGS. 21A, 21B, 21C, 21D, 21E and 21F are perspective views illustrating alternative configurations of bone fixation/fusion devices of a type shown in FIG. 18A.
Figure 21B:
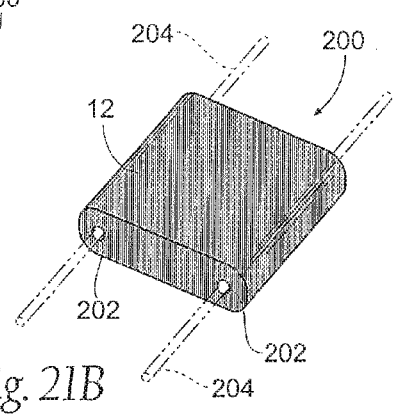
Figure 21C:
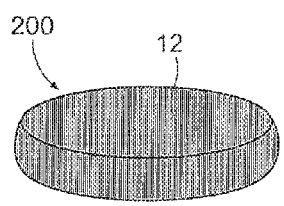
Figure 21D:
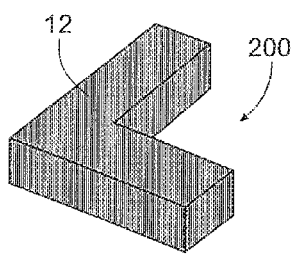
Figure 21E:
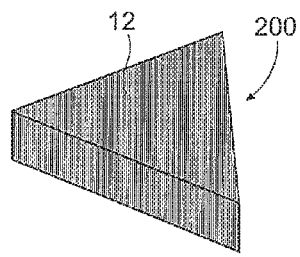
Figure 21F:
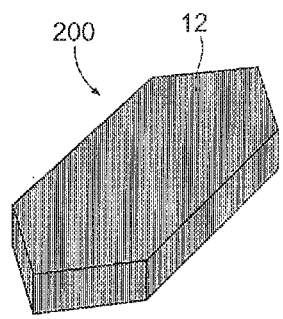

The size and configuration of the bone fixation/fusion device 200 may be modified or adjusted in diverse ways to serve the intended stabilization function in diverse bone locations, bone geometries, or bone types, which are intended to be fused or repaired. The bone fixation/fusion device 200 can come in a family of different pre-established sizes and shapes, or it can be individually sized and configured to meet the requirements of a particular individual's anatomy. For the sake of illustration, by not limitation, a given bone fixation/fusion device 200 may take the form of a disc (FIG. 21A), a square (FIG. 21B), or an oval (FIG. 21C). The height, width, and length of a given bone fixation/fusion device 200 may be varied depending on the specific location and amount of bone to be crossed for stabilization. A given bone fixation/fusion device may possess a symmetric geometry, or an asymmetric or complex geometry—such as an L shape (FIG. 21D), a triangle (FIG. 21E), or rectangle with a triangular ends (FIG. 22F). Any combination of linear or curvilinear or rounded geometries is possible.

Figure 24:
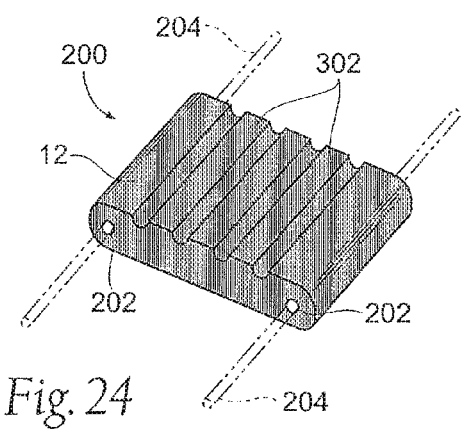
FIG. 24 is a perspective view illustrating an alternative embodiment of the bone fixation/fusion device of a type shown FIG. 18A in which the device includes a series of grooves providing an anti-rotational function.

As before described, a given bone fixation/fusion device can be cannulated to aid in guidance during placement or implantation. For example, as shown in FIGS. 18A and 18B, the device 200 can include a pair of opposing guide bores 202. The guide bores 202 are sized and configured to accommodate passage of guide pins 204, which are secured at the intended site of device placement. Other forms of cannulated devices 200 are shown in FIGS. 21B and 24. In this way, the bone fixation/fusion device 200 can be guided by the pins 204 to the intended bone placement site.

Figure 22A:
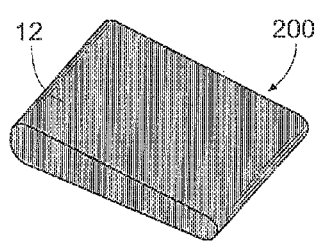
FIGS. 22A and 22B are perspective views illustrating alternative embodiments of the bone fixation/fusion of a type shown in FIG. 18A in which the device is profiled.
Figure 22B:
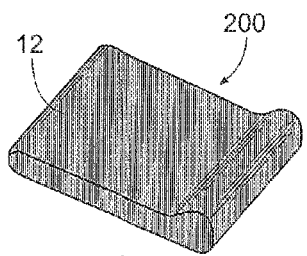

To aid in stabilizing a given bone fixation/fusion device within bone, the device may be profiled. For example, as shown in FIG. 22A, the bone fixation/fusion device 200 may vary in height across its entire length of the device 200, to form a tapered wedge. Alternatively, as shown in FIG. 22B, the bone fixation/fusion device 200 may vary in height at one end only. In these arrangements, the bone fixation/fusion device 200 is desirably positioned with the area of greatest height in the proximal direction, which serves to wedge the device 200 into place within bone.

Figure 23A:
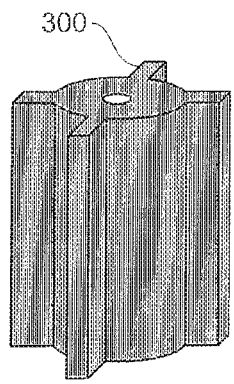
FIGS. 23A and 23B are perspective views illustrating alternative embodiments of the bone fixation/fusion device of a type shown in FIG. 1 with structural elements that provide an anti-rotational function.
Figure 23B:
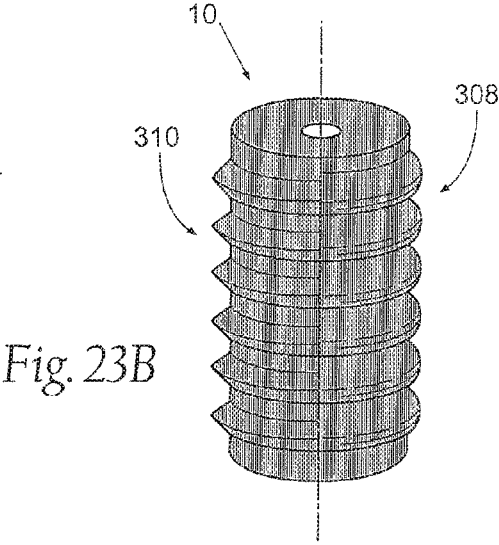
Figure 25:
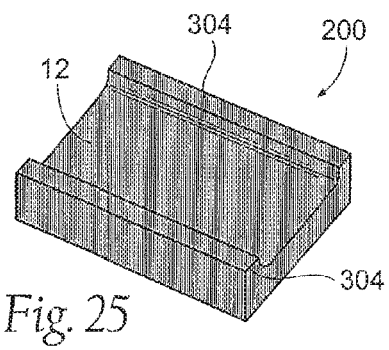
FIG. 25 is a perspective view illustrating an alternative embodiment of the bone fixation/fusion device of a type shown in FIG. 18A in which the device includes a pair of opposing wings providing an anti-rotational function.
Figure 26:
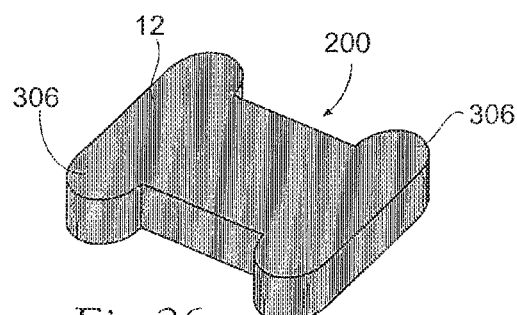
FIG. 26 is a perspective view illustrating an alternative embodiment of the bone fixation/fusion device of FIG. 18A in which the device includes a pair of opposing flanges providing an anti-rotational function.

To also aid in stabilizing a given bone fixation/fusion device within bone, the device can include one or more anti-rotational elements, which further stabilize and secure the device in the desired position within bone. The size and configuration of the anti-rotational elements may vary. For example, the anti-rotational elements may comprise an array of fins 300 projecting from a stem-like device 10 (FIG. 23A), or an array of grooves 302 formed in a rectangular wafer device 200 (FIG. 24), or wings 304 formed in a rectangular wafer device 200 (FIG. 25), or flanges 306 projecting from a wafer device 200 (FIG. 26). The anti-rotational elements can comprise (see FIG. 23B) an array of bumps 308 or surface projections 310 formed on all or a portion of the device, which can be either stem-like or wafer-like in its configuration. Any number of anti-rotational elements, or any configuration of anti-rotational elements, or any combinations of configurations can be provided to serve the functional objective of stabilization.

Figure 27:
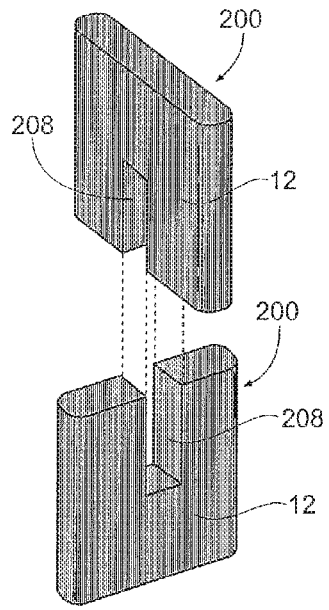
FIG. 27 is an exploded view of a pair of coupled bone fixation/fusion devices that, when fitted together, form a composite bone fixation/fusion device.
Figure 28:
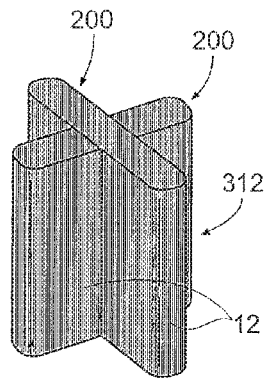
FIG. 28 is an assembled view of the composite bone fixation/fusion device formed from the assembly of the bone fixation/fusion devices shown in FIG. 27.
Figure 29:
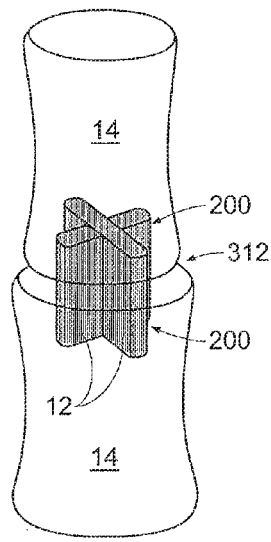
FIG. 29 is a front view of the assembled composite bone fixation/fusion device of FIG. 28 positioned in association with a fracture line or between different bone segments.

As also previously described, two or more bone fixation/fusion devices 200 of the types generally described above may be assembled to form a composite bone fixation/fusion device having a desired size and configuration. For example, in the arrangement shown in FIGS. 27 to 29, the bodies of two bone fixation/fusion devices 200 each have a slot 208. Slot 208 in a first device 200 mates with a like or complementary slot 208 in a second device 200 to permit the assembly of a composite bone fixation/fusion device 310, which has a crossed, anti-rotational configuration for placement across bone segments 14. The crossed relation of the composite bone fixation/fusion device 310 has an increased surface area and adds further stability to the devices 200 in bone during the fusion process.

It will be apparent to one of skill in the art that the location, size, and configuration of the slots 208 may be varied to accommodate specific needs and a specific anatomical location as well as individual anatomy. It is also apparent that other mating configurations, e.g., groove and tab fitments, or snap-fit arrangements, or Morse taper fits, or threaded assemblies, can be used to assemble two or more bone fixation/fusion devices into a composite device 310.

Figure 30:
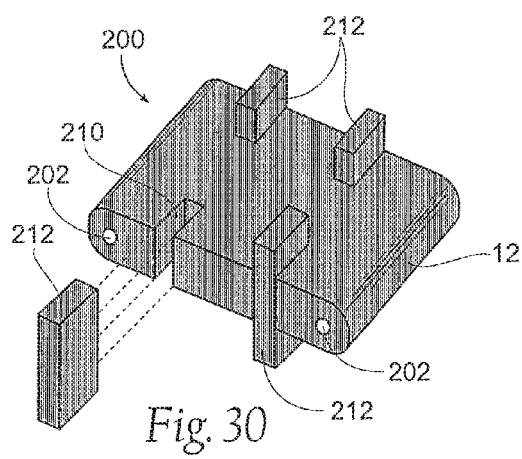
FIG. 30 is a perspective view of an alternative embodiment of the bone fixation/fusion device of a type shown in FIG. 18A with fixation plates.

As shown in FIG. 30, fixation or gripping plates 212 may be fitted to a given bone fixation/fusion device. In the arrangement shown in FIG. 30, the body of the bone fixation/fusion device 200 includes one or more attachment sites 210, e.g., slits or indentations, which are sized and configured to receive a selectively removable fixation or gripping plate 212. When received within the slit 210, the plate 212 extends radially from the device to grip into bone and further secure the device 200 within bone.

Figure 31:
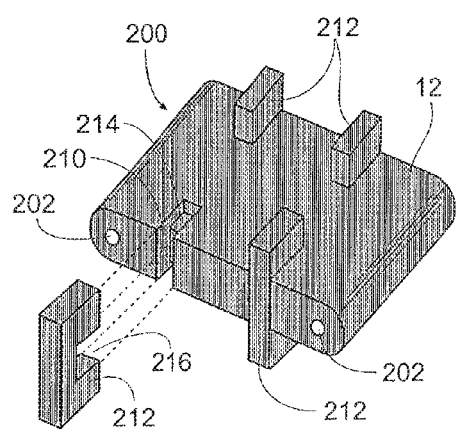
FIG. 31 is a perspective view of an alternative embodiment of the bone fixation/fusion device of FIG. 30.

In an alternative embodiment, shown in FIG. 31, the attachment site 210 can include a tab 214, which mates with a notch 216 in the fixation plate 212 to secure the plate 212 within the device 200.

Other forms of interlocking or nesting configuration can be used. For example, tongue-and-groove fitments, or snap-fit arrangements, or threaded fitments, or Morse taper assemblies can be used to assemble one or more fixation or gripping plates to a bone fixation/fusion device.

The fixation or gripping plate 212 is formed of durable biocompatible metal or bone substitute material, as previously described. In some cases, it may be desirable to provide a bony in-growth surface on at least a portion of the plate 212. Alternatively, the plate 212 may be formed of a bioabsorbable material, as already described.

Figure 32:
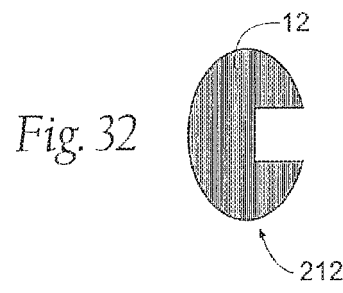
FIG. 32 is a side view of an alternative embodiment of a fixation plate having a rounded configuration.
Figure 33:
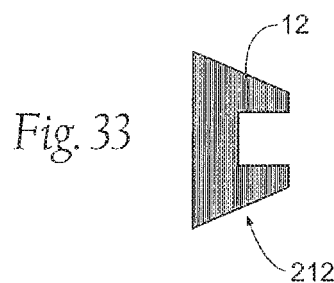
FIG. 33 is a side view of an alternative embodiment of a fixation plate having a tapered configuration.

FIGS. 30 and 31 illustrate embodiments in which the plates 212 present a generally blunt and flat configuration. It will be apparent to one of skill in the art that, however, that the plates 212 may also provide a sharpened or cutting edge or be otherwise sized and configured as necessary to accommodate specific location and individual anatomy. For example, the plate 212 may be rounded (FIG. 32) or tapered (FIG. 33).

Figure 34:
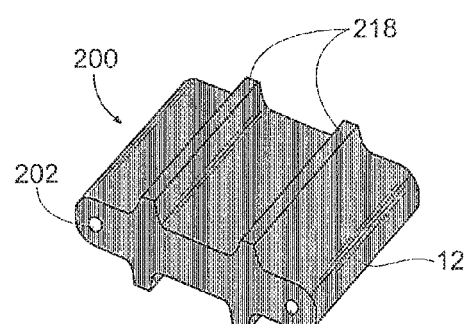
FIG. 34 is a perspective view of an alternative embodiment of the bone fixation/fusion device of a type shown in FIG. 18A providing a series of radially-extending fixation ridges.

FIG. 34 illustrates an alternative embodiment in which one or more fixation ridges 218 extend radially from the bone fixation/fusion device 200. Similar to the fixation plates 212, the ridges 218 may be variously sized and configured so as to grip into bone and further secure the bone fixation/fusion device 200 within bone.

Figure 35A:
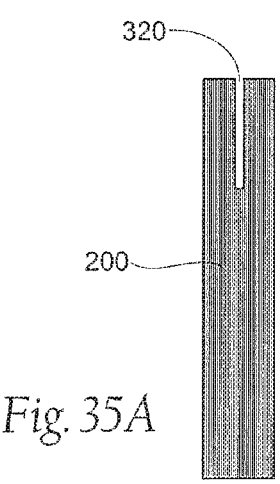
FIGS. 35A and 35B are perspective views of a bone fixation/fusion device having a malleable region that can be flared or expanded to provide fixation and/or anti-rotation resistance.
Figure 35B:
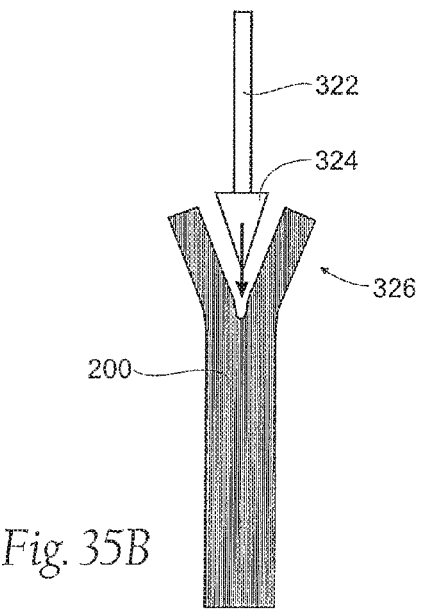

Fixation elements can be formed in situ. For example, as shown in FIG. 35A, a bone fixation/fusion device 200 can include a malleable region 320 that normally presents a low-profile conducive to implantation. As FIG. 35B shows, the profile of the malleable region 320 can be changed in situ after implantation to a radially enlarged or extended profile 326 that provides stabilization or an anti-rotational function to the device 200. In the illustrated embodiment, the malleable region 320 is slotted (see FIG. 35A) to accommodate placement of a wedge tool 324 carried for manipulation by a stylet or cannula 322 (see FIG. 35B). The wedge tool 324 flays apart the slotted malleable region 320 (as FIG. 35B shows), to create the enlarged profile 326 for stabilization and/or rotation resistance.

Figure 36:
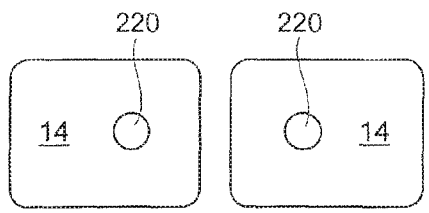
FIG. 36 is a front plan view illustrating the drilling of pilot holes in adjacent bone segments, which can comprise a fracture line in the same bone or different bone segments.

In use, and with reference to FIG. 36, pilot holes 220 are drilled into adjacent bone segments 14 (e.g., along a fracture line in a single bone or between adjacent segments of different bones) by conventional surgical techniques. In the illustrated embodiment, a single pilot hole 220 is drilled into each bone segment 14. It is to be understood that the number and configuration of the pilot holes 220 may vary as necessary or as desired.

Figure 37:
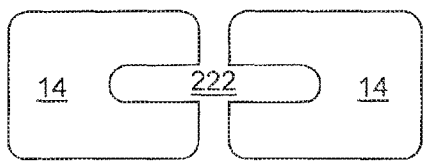
FIG. 37 is a front plan view illustrating a cavity bored between the pilot holes to receive a bone fixation/fusion device.

As shown in FIG. 37, the physician can then saw, using conventional methods, between the pilot holes 220 to prepare a cavity 222 to receive the device 200.

Figure 38:
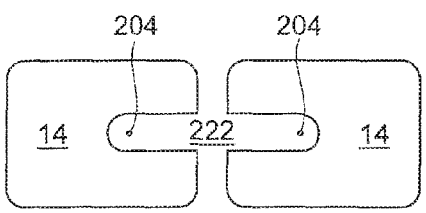
FIG. 38 is a front plan view illustrating the placement of a pair of guide pins within the bored cavity.
Figure 39:
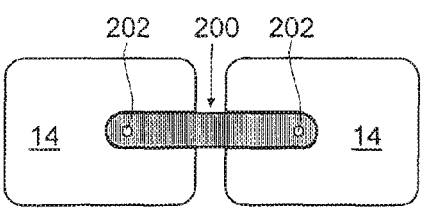
FIG. 39 is a front plan view illustrating the placement of the bone fixation/fusion device into the cavity and removal of the guide pins.

Guide pins 204 may, if desired, be placed at opposing ends of the bored cavity 222, as seen in FIG. 38. In this arrangement, as shown in FIG. 39, the selected bone fixation/fusion device 200 is passed over the guide pins 204 to position the device 200 with the cavity 222. The guide pins 204 may then be removed. In an alternative arrangement, guide pins 204 need not be used, and the device 200 is manually inserted by the physician into the bore cavity 222.

Figure 40:
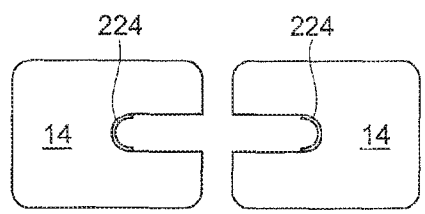
FIG. 40 is a front plan view illustrating the placement of a pair of opposing c-shaped restraints within the bored cavity.
Figure 41:
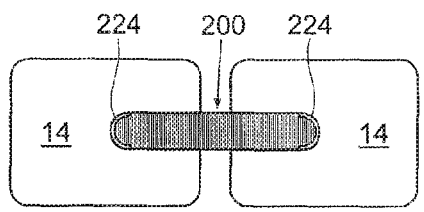
FIG. 41 is a front plan view illustrating the placement of the bone fixation/fusion device into the cavity within the restraints.

An alternative embodiment is illustrated in FIGS. 40 and 41. In this embodiment, a c-shaped restraint 224 is placed against each end of the bored cavity 222. The selected bone fixation/fusion device 200 is then positioned between the restraints 222 such that the restraints 222 engage the device 200 to secure the device 200 within bone.

Figure 42:
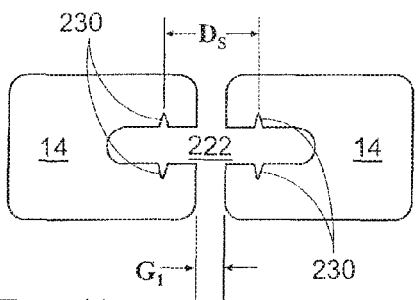
FIG. 42 is a front plan view illustrating a bone cavity like that shown in FIG. 37 to receive a bone fixation/fusion device, the bone cavity in FIG. 42 showing the inclusion of slots to receive fixation ridges formed on the bone fixation/fusion device, as shown in FIG. 43.
Figure 43:
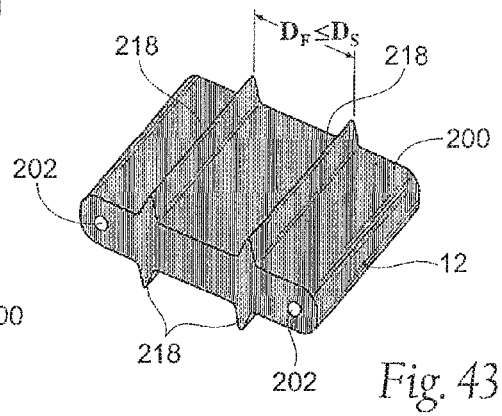
FIG. 43 is a perspective view of a bone fixation/fusion device like that shown in FIG. 34 providing a series of radially-extending fixation ridges.

When the bone fixation/fusion device 200 includes one or more fixation ridges or fins 218 (as shown in FIG. 34 and again in FIG. 43), slots 230 can be sawed or cut within the bored cavity 222 using conventional tools, as FIG. 42 shows. The slots 230 are sized and configured so that the ridges 218 nest with the slots 230, to fixate the ridges 218 and thus the fixation/fusion device 200 within and between the adjacent bone segments 14. The nesting relationship between the ridges 218 and the slots 230 put the adjacent bone segments into compression, at least resisting further enlargement of the distance between them.

Figure 44:
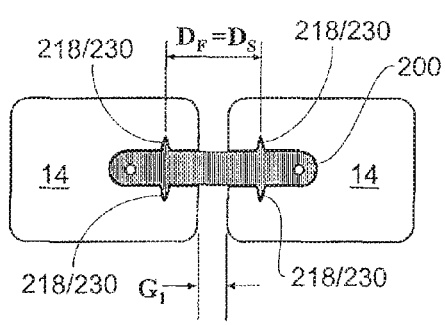
FIG. 44 is a front plan view showing placement of the bone fixation/fusion device shown in FIG. 43 in the slotted bone cavity shown in FIG. 42, with the distance between the bone slots being generally equal to the distance between the fixation ridges.

As FIG. 42 shows, the slots 230 are formed in a spaced-apart relationship within the respective bone segments 14, at a distance designated $D_S$ in FIG. 42. The distance $D_S$ takes into account the distance between the fixation ridges of the device 200, designated $D_F$ in FIG. 42. Desirably, $D_F$ is at least generally equal to and is not substantially greater than $D_S$. In this way, the distance between the adjacent bone segments 14, designated $G_1$ in FIG. 42 (which can comprise a fracture line in a single bone or a gap between adjacent segments of different bone), is not enlarged by the presence of the device 200. This outcome is shown in FIG. 44, where $D_F$ is generally equal to $D_S$. As FIGS. 42 and 44 show, the interval $G_1$ between the adjacent bone segments 14 before installation of the device 200 (FIG. 42) is generally the same after installation of the device 200 (FIG. 44).

Figure 45:
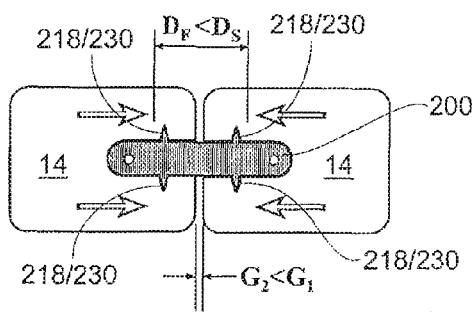
FIG. 45 is a front plan view showing placement of the bone fixation/fusion device shown in FIG. 43 in the slotted bone cavity shown in FIG. 42, with the distance between the bone slots being generally greater than the distance between the fixation ridges, to apply compression between adjacent bone segments.

In certain instances, it may be desirable to make the distance $D_S$ between the slots 230 slightly larger (e.g., from about at least 0.5 mm to about 3 mm farther apart) than the distance $D_F$ between the ridges 218. This arrangement is shown in FIG. 45. In this arrangement, when the device 200 is introduced, the ridges 218 serve to pull the adjacent bone segments closer together, while also applying compression to maintain this condition (as shown by arrows in FIG. 45). As FIGS. 42 and 45 show, the interval $G_2$ between the adjacent bone segments 14 after installation of the device 200 (FIG. 45) is smaller than the interval $G_1$ before installation of the device 200 (FIG. 42).

Figure 46:
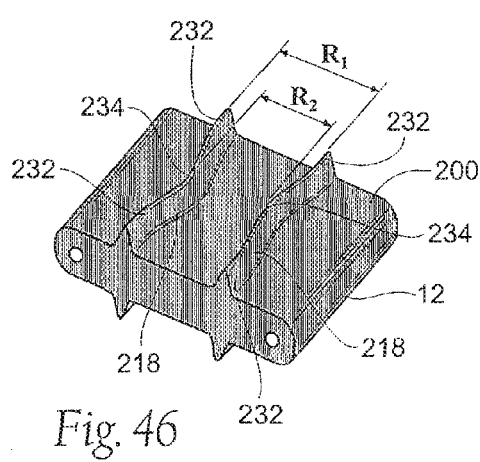
FIG. 46 is a perspective view of a bone fixation/fusion device like that shown in FIG. 43 providing a series of radially-extending fixation ridges having curvilinear portions.

The ridges 218 shown in the preceding embodiments (see, e.g., FIGS. 34 and 43) are generally uniformly linear in configuration. As shown in FIG. 46, the ridges 218 can be non-uniform and curvilinear in configuration, meaning that the ridges 218 can include portions that curve or are otherwise not uniformly straight. The curvilinear configuration can vary.

FIG. 46 shows, as one representative embodiment, curvilinear ridges 218, each of which includes generally linear end portions 232 and a curved, non-linear (curvilinear) intermediate portion 234. The distance $R_1$ between the linear end portions 232 is greater than the distance $R_2$ between the curved intermediate portion 234. As FIG. 46 shows, the curved portions 234 generally face inward toward the centerline of the device 200 in a symmetric fashion. It should be appreciated, that an asymmetric arrangement between the linear and curved portions 232 and 234 among the ridges 218 can be used.

Figure 47:
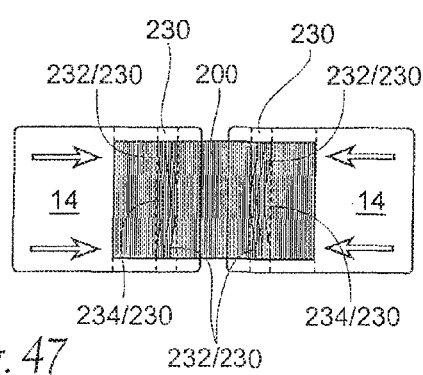
FIG. 47 is a top view showing placement of the bone fixation/fusion device shown in FIG. 46, with curvilinear ridges, in a slotted bone cavity like that shown in FIG. 42.

In use, as FIG. 47 shows, the curvilinear ridges 218 nest within the formed slots 230, which can themselves be more easily formed in bone in a linear fashion. Within the linear slots 230, the undulating curved portions 234 of the curvilinear ridges 218 abut against or otherwise extend closer to the walls the formed linear slots 234 than the linear portions 232. The presence of curvilinear ridges 218 reduces or prevents "play" or lateral shifting of the device 200 within the bone cavity 222 after being placed in adjacent bone segments 14. The curvilinear ridges 218 stabilize or fixate placement of the device 200 within the bone cavity 222, accommodating differences in dimensional tolerances that may exist between the ridges 218 on the device 200 and slots 230 formed in the bone cavity 222. The curvilinear ridges 218 also serve to augment compression (shown by arrows in FIG. 47) between the adjacent bone segments 14, to establish and maintain a desired relationship between them for fusion or fixation purposes.

Figure 48:
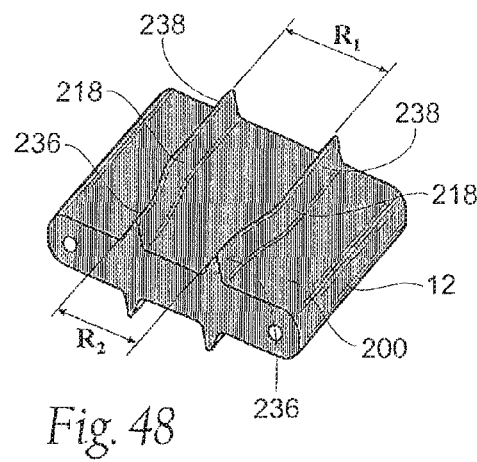
FIG. 48 is a perspective view of a bone fixation/fusion device like that shown in FIG. 46 providing a series of radially-extending fixation ridges having curvilinear portions.

FIG. 48 shows, as another representative embodiment, curvilinear ridges 218, each of which includes a generally linear first end portion 236 and a non-linear, curved (curvilinear) second end portion 238. The distance $R_1$ between the linear first end portions 236 is greater than the distance $R_2$ between the curved second end portion 238. In FIG. 48, the curved end portions 236 extend generally inward toward the centerline of the device 200 in a symmetric fashion. Again, it should be appreciated that an asymmetric arrangement of linear and curvilinear portions among the ridges 218 can be used.

Figure 49:
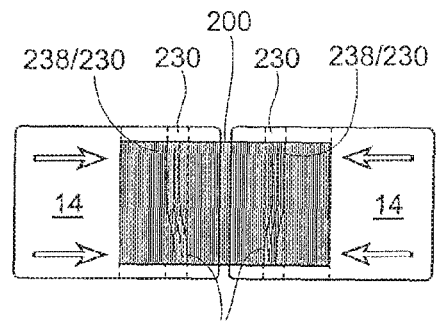
FIG. 49 is a top view showing placement of the bone fixation/fusion device shown in FIG. 48, with curvilinear ridges, in a slotted bone cavity like that shown in FIG. 42.

In use, as FIG. 49 shows, when the curvilinear ridges 218 nest within the formed linear slots 230, the undulating curved end portions 238 abut against or otherwise extend closer to the walls the formed linear slots 230 than the linear end portions 236. As in FIG. 47, the presence of curvilinear ridges 218 in the arrangement shown in FIG. 49 reduces or prevents "play" or lateral shifting of the device 200 within the formed linear slots 230. The curvilinear ridges 218 also apply and maintain compression between the adjacent bone segments 14 to establish and maintain a desired relationship between them (as shown by arrows in FIG. 49).

Figure 50:
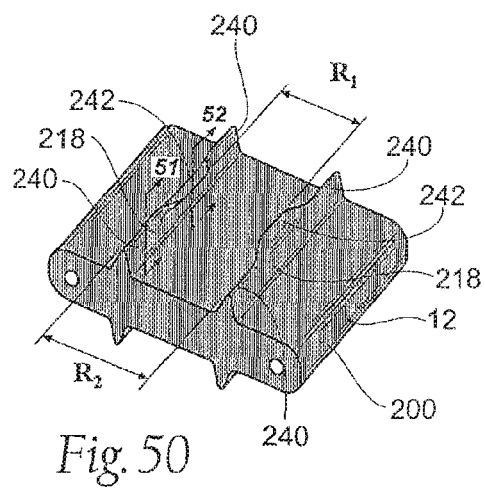
FIG. 50 is a perspective view of a bone fixation/fusion device like that shown in FIG. 46 providing a series of radially-extending fixation ridges having curvilinear portions.
Figure 51:
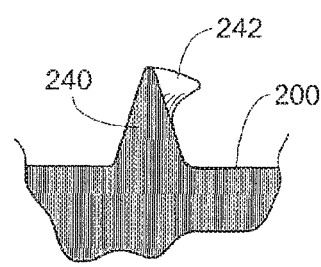
FIG. 51 is a side section view taken generally along line 51-51 in FIG. 50, showing a ridge portion with a generally vertical draft.
Figure 52:
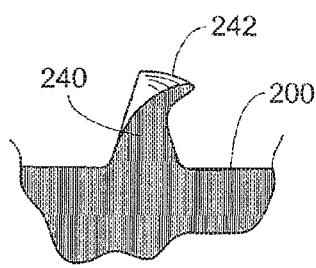
FIG. 52 is a side section view taken generally along line 52-52 in FIG. 50, showing a ridge portion with a more horizontal or angled draft, comprising a curvilinear ridge portion.

FIG. 50 shows another representative embodiment of curvilinear ridges 218. In FIG. 50, the draft of the ridges 218 changes between a vertical draft 240 on the end portions of the ridges 218 (see FIG. 51) to a more horizontal or angular draft 242 on the intermediate portion of the ridges 218 (see FIG. 52). The more horizontal or angular drafts 242 face inward toward the centerline of the device 200, however, the drafts 242 could face in an opposite direction away from the centerline, and in an asymmetric way. As configured in FIG. 50, the distance $R_1$ between the vertical drafts 240 of the ridges 218 is greater than the distance $R_2$ between the more horizontal drafts 242 of the ridges.

Figure 53:
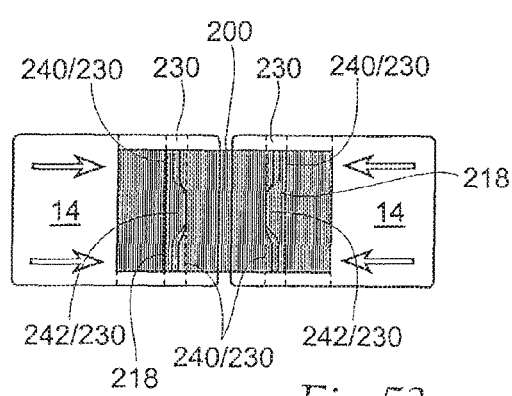
FIG. 53 is a top view showing placement of the bone fixation/fusion device shown in FIG. 50, with curvilinear ridges, in a slotted bone cavity like that shown in FIG. 42.

In use, as FIG. 53 shows, when the curvilinear ridges 218 nest within the formed linear slots 230, the more horizontal drafts 242 abut or otherwise rest closer to the walls the formed linear slots 230 than the vertical drafts 240. As previously described in the context of FIGS. 47 and 49, the presence of different curvilinear ridge drafts 240 and 242 in the arrangement shown in FIG. 53 reduces or prevents lateral "play" or shifting of the device 200 within the formed linear slots 230 due, e.g., to differences in dimensional tolerances among the ridges 218 on the device 200 and slots 230 formed in the bone cavity 222. The curvilinear ridges 218 formed by the different drafts 240 and 242 also apply and maintain compression between the adjacent bone segments to establish and maintain a desired relationship between them (as shown by arrows in FIG. 53).

Figure 54:
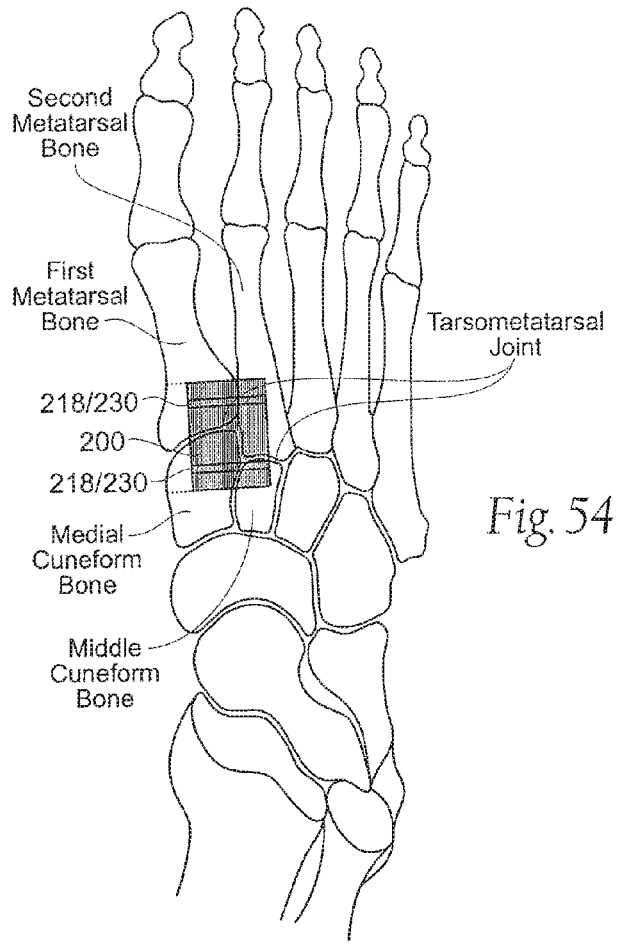
FIG. 54 is a superior anatomic view of a human foot, showing the placement of a bone fixation/fusion device of a type shown in FIG. 43 in a bone cavity in the first and second metatarsal bones, medial and middle cuneiform bones, and spanning the tarsometatarsal joint.
Figure 55:
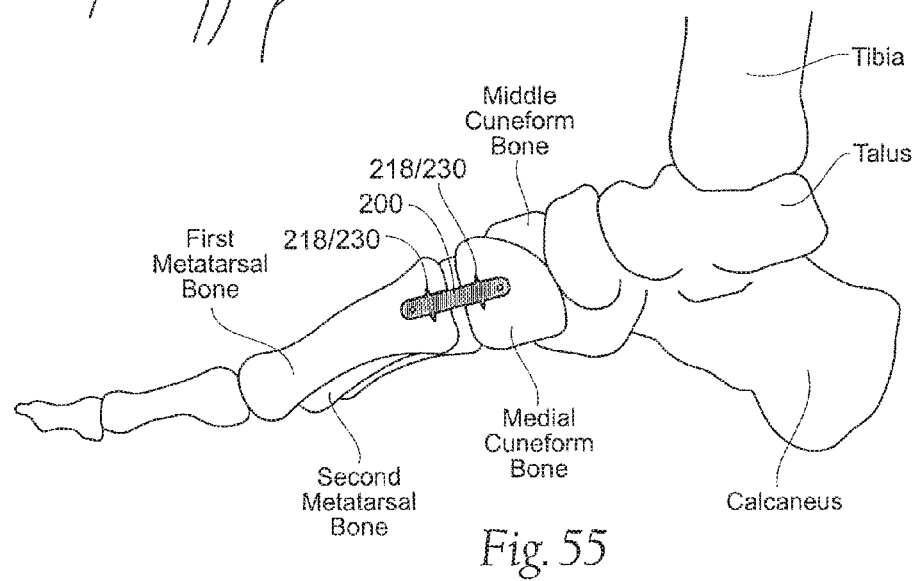
FIG. 55 is a medial side view of the human foot shown in FIG. 54.

FIGS. 54 and 55 show anatomic views of a representative placement of the bone fixation/fusion device 200 as previously described. In FIGS. 54 and 55, the device 200 is placed between adjacent bone segments comprising the first and second metatarsal bones and the medial and middle cuneiform bones. In this arrangement, the device 200 also spans portion of the tarsometatarsal joint. The presence of the device 200 serves to fixate these adjacent bone segments and fuse the joint. In FIGS. 54 and 55, the device 200 includes fixation ridges 218 as previously described; however, devices 200 without ridges 218, or with curvilinear ridges, can be used for this purpose as well.

Figure 56:
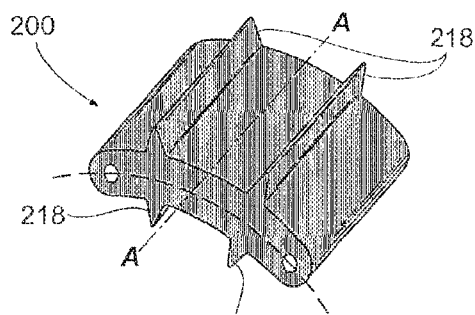
FIG. 56 is a perspective view of a bone fixation/fusion device like that shown in FIG. 43 showing the flexibility of the bone fixation/fusion device about an axis A.
Figure 57:
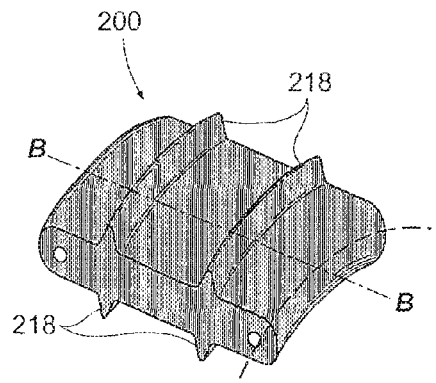
FIG. 57 is a perspective view of a bone fixation/fusion device like that shown in FIG. 43 showing the flexibility of the bone fixation/fusion device about an axis B.

In many cases it is desirable that the device 200 be flexible. It may be desired that the device 200 is flexible about an axis A which extends across the width of the device and is generally parallel to the fracture line or gap between bones to be fused (see FIG. 56). It may also be desired that the device 200 is flexible about an axis B which extends across the length of the device and is generally perpendicular to the fracture line or gap (see FIG. 57). It may also be desirable that the device 200 be flexible about both axes. Various configurations may be used to achieve flexibility.

Figure 58:
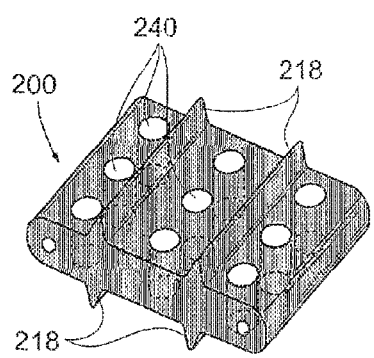
FIG. 58 is a perspective view of a bone fixation/fusion device like that shown in FIG. 43 providing a plurality of holes extending perpendicularly through the bone fixation/fusion device from the top to the bottom.
Figure 59:
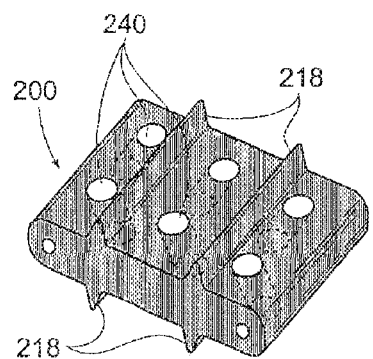
FIG. 59 is a perspective view of a bone fixation/fusion device like that shown in FIG. 43 providing a plurality of holes extending angularly through the bone fixation/fusion device from the top to the bottom.
Figure 60:
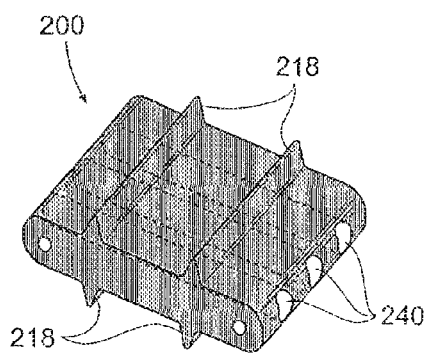
FIG. 60 is a perspective view of a bone fixation/fusion device like that shown in FIG. 43 providing a plurality of holes extending perpendicularly through the bone fixation/fusion device from one side to the other.
Figure 61:
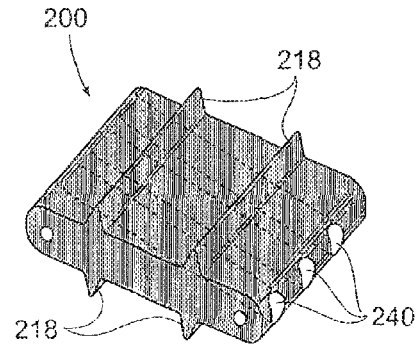
FIG. 61 is a perspective view of a bone fixation/fusion device like that shown in FIG. 43 providing a plurality of holes extending angularly through the bone fixation/fusion device from one side to the other.

The device 200 may be formed with a plurality of holes 240 extending through the device. Various hole 240 configurations may be used to achieve the desired flexibility. The holes 240 can extend through the device 200 from the top to the bottom, perpendicular to the top surface as shown in FIG. 58. The holes 240 can extend from the top of the device 200 to the bottom of the device at an angle as shown in FIG. 59. The holes 240 can extend from one side of the device 200 to the opposite side, perpendicular to the surface of the side as shown in FIG. 60. The holes 240 can extend through the device 200 at an angle as shown in FIG. 61.

Figure 62:
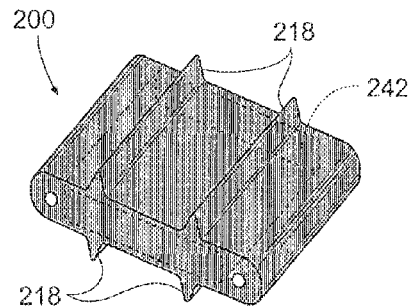
FIG. 62 is a perspective view of a bone fixation/fusion device like that shown in FIG. 43 providing a hollow cavity within the bone fixation/fusion device.
Figure 67:
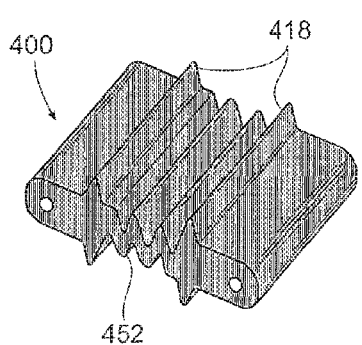
FIG. 67 is a perspective view of a bone fixation/fusion device like that shown in FIG. 43 providing a hollow cavity within the bone fixation/fusion device, and further including an accordion-like section to increase the flexibility of the device.

Alternatively, as shown in FIG. 62, the device 200 can be formed with a hollow cavity 242 to increase the flexibility of the device 200. As shown in FIG. 67, the device 400 can be formed with an accordion-like section 452 to increase the flexibility of the device 400.

Figure 63:
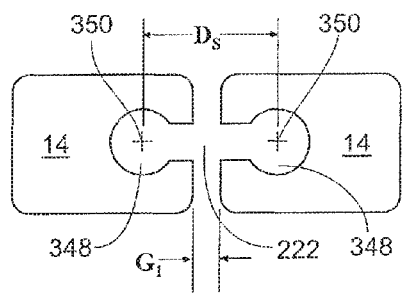
FIG. 63 is a front plan view illustrating a bone cavity like that shown in FIG. 42 to receive a bone fixation/fusion device, the bone cavity in FIG. 63 showing the inclusion of cylindrical end apertures to receive the cylindrical end caps formed on the bone fixation/fusion device, as shown in FIG. 64.
Figure 64:
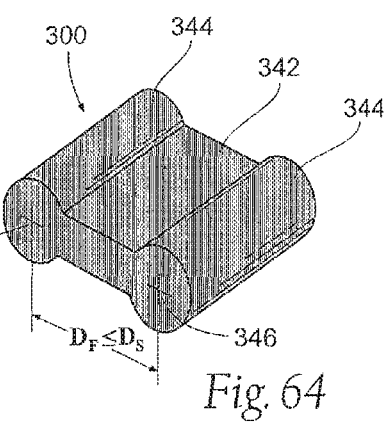
FIG. 64 is a perspective view of a bone fixation/fusion device like that shown in FIG. 43 providing a pair of cylindrical end caps.
Figure 65:
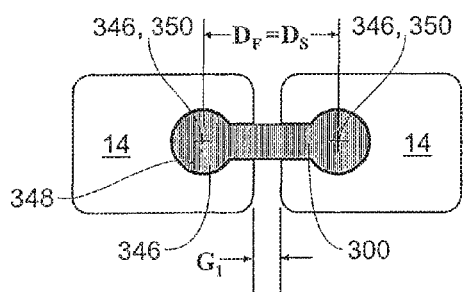
FIG. 65 is a front plan view showing placement of the bone fixation/fusion device shown in FIG. 64 in the cavity shown in FIG. 63, with the distance between the center points of the cylindrical end apertures being generally equal to the distance between center points of the cylindrical end caps.

As FIG. 64 shows, the bone fixation/fusion device 300 can have a rod-like configuration. In this embodiment, the device 300 includes a central rectangular portion 342 formed with two cylindrical end caps 344. Each cylindrical end cap 344 has a center point 346 (see FIG. 64). The distance between end cap center points 346 is designated as $D_F$. The device 300 fits in a slot 222 cut in two bone segments 14 in generally the same manner as is described above. The slot 222 is cut with a cylindrical end aperture 348 at each end of the slot 222. Each cylindrical end aperture 348 has a center point 350 (see FIG. 63). The distance between these aperture center points 350 is designated as $D_S$. Desirably, $D_S$ at least generally equal to and is not substantially greater than $D_F$. In this manner, the distance between the adjacent bone fragments is not enlarged by the presence of the device 300. This is shown in FIG. 65, where $D_S$ is approximately equal to $D_F$. As shown in FIGS. 63 and 65, the interval $G_1$ between the adjacent bone segments 14 before installation of the device 300 is the same as after installation of the device 300.

Figure 66:
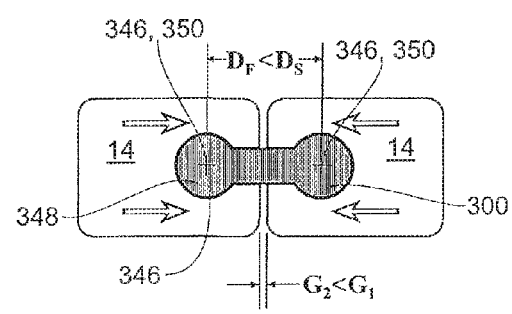
FIG. 66 is a front plan view showing placement of the bone fixation/fusion device shown in FIG. 64 in the cavity shown in FIG. 63, with the distance between the center points of the cylindrical end apertures being generally greater than the distance between the center points of the cylindrical end caps, to apply compression between adjacent bone segments.

In some instances it may be desirable to make the distance $D_S$ between the aperture center points 350 slightly larger than the distance $D_F$ between the end cap center points 346. This arrangement is shown in FIG. 66. In this arrangement, when the device 300 is introduced, the cylindrical end caps 344 serve to pull the adjacent bone segments 14 together, while also applying compression to maintain this condition (as shown by arrows in FIG. 66). As FIGS. 63 and 66 show, the interval $G_1$ between the bone segments before installation of the device 300 is greater than the interval $G_2$ after installation of the device 300.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A method for the fixation or fusion of a first bone segment to a second bone segment across a joint, the method comprising:

providing an elongate implant having a proximal end, a distal end, a longitudinal axis, a lumen extending through the elongate implant along the longitudinal axis, and a cross-sectional profile transverse to the longitudinal axis that is defined by at least one apex, wherein the elongate implant is free from external screw threads; and inserting the elongate implant through the first bone segment and transversely across the joint and into the second bone segment by applying an axially directed force to the elongate implant, such that the distal end of the elongate implant is inserted into the second bone segment and the proximal end of the elongate implant remains within the first bone segment;

wherein the first bone segment and/or the second bone segment is a vertebra.

2. The method of claim 1, wherein the elongate implant comprises at least two apices.

3. The method of claim 1, wherein the elongate implant comprises at least three apices.

4. The method of claim 1, wherein the elongate implant further comprises one or more anti-rotational elements that projects radially outwards relative to the longitudinal axis.

5. The method of claim 1, wherein the elongate implant further comprises one or more fenestrations.

\* \* \* \* \*